United States Patent [19]

Konoki et al.

[11] 4,334,096

[45] Jun. 8, 1982

[54] PROCESS FOR SYNTHESIZING UREA

[75] Inventors: Keizo Konoki, Tokyo; Michio Nobue, Funabashi; Akito Fukui, Yotsukaidomachi; Shigeru Inoue, Kamakura, all of Japan

[73] Assignees: Toyo Engineering Corporation; Mitsui Toatsu Chemicals, Inc., both of Tokyo, Japan

[21] Appl. No.: 191,212

[22] PCT Filed: Jul. 24, 1979

[86] PCT No.: PCT/JP79/00192

§ 371 Date: Mar. 24, 1980

§ 102(e) Date: Mar. 5, 1980

[87] PCT Pub. No.: WO80/00343

PCT Pub. Date: Mar. 6, 1980

[30] Foreign Application Priority Data

Jul. 24, 1978 [JP] Japan ................................ 53-90120

[51] Int. Cl.³ .......................................... C07C 126/02
[52] U.S. Cl. ...................................................... 564/72
[58] Field of Search .............................. 564/72, 71, 70

[56] References Cited

U.S. PATENT DOCUMENTS 3,471,558 10/1969 Wentworth et al. ................. 564/72
3,607,938 9/1971 Braun ................................ 564/72 X
3,984,469 10/1976 Guadalupi et al. ................... 564/72
4,137,262 1/1979 Guadalupi et al. ................... 564/72

FOREIGN PATENT DOCUMENTS 757274 10/1970 Belgium ................................ 564/72
1468245 12/1968 Fed. Rep. of Germany ........ 564/72
1814480 7/1969 Fed. Rep. of Germany ........ 564/72

Primary Examiner—John Doll
Attorney, Agent, or Firm—Blanchard, Flynn, Thiel, Boutell & Tanis

[57] ABSTRACT

In the process for urea synthesis, an effluent from a reactor 2 containing urea, ammonium carbamate, excess ammonia and water is introduced in a first heater 3 to separate excess ammonia and to decompose ammonium carbamate, thereby separating them from the liquid phase; then the liquid effluent from the first heater 3 is introduced in a second heater 6 to separate the remaining excess ammonia and to decompose ammonium carbamate in the presence of starting carbon dioxide used as stripping gas, thereby separating them from the liquid phase; the liquid effluent from the second heater 6 is introduced into a urea solution purification step in which pressure is lower than in the above step; and the separated gaseous effluents from the first and the second heaters are returned into the reactor.

10 Claims, 2 Drawing Figures

PROCESS FOR SYNTHESIZING UREA

FIELD OF THE INVENTION

The present invention relates to a process for synthesizing urea.

More particularly, the present invention relates to a process wherein the production cost of urea is reduced by efficiently returning reactants not converted to urea in the urea synthesis reaction into the reactor for the urea synthesis.

DESCRIPTION OF THE PRIOR ART

In the production of urea, the starting materials, i.e., ammonia and carbon dioxide, are substantially quantitatively converted to ammonium carbamate under usual reaction conditions, for example, comprising a pressure of 200 Kg/cm² and a temperature of 190° C., in the presence of excess ammonia, as shown in reaction formula (1). Ammonium carbamate is further converted to urea as shown in reaction formula (2) wherein the equilibrium conversion is determined by the reaction conditions and the actual conversion is determined by the rate of attaining the equilibrium conversion, which rate depends on the residence time in the reaction zone:

$$2NH_3 + CO_2 \rightleftharpoons NH_2COONH_4 \tag{1}$$

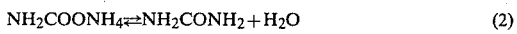
$$NH_2COONH_4 \rightleftharpoons NH_2CONH_2 + H_2O \tag{2}$$

The actual conversion is about 50–75% industrially.

Namely, the excess ammonia and about 25–50%, based on the theoretical amounts, of the starting materials ammonia and carbon dioxide remain unconverted to urea.

A known process for separating urea from unconverted materials comprises heating an effluent from the reaction zone under reduced pressure to decompose ammonium carbamate into ammonia and carbon dioxide, thereby separating them in the form of a gas together with the excess ammonia, absorbing the ammonia and carbon dioxide in a recovered liquid formed in the subsequent step of decomposing and absorbing ammonium carbamate under a lower pressure, and returning the recovered liquid into the reaction zone.

Another known process comprises stripping an effluent from the reaction zone by subjecting it to gas-liquid contact with gaseous starting materials, ammonia or carbon dioxide, under a pressure which is substantially not reduced, thereby decomposing and separating unconverted ammonium carbamate and returning the decomposition products into the reaction zone. This process utilizes the fact that an effect equivalent to that obtained by pressure reduction is obtained by the gas-liquid contact.

SUMMARY OF THE INVENTION

The process of the present invention has been attained by comparison and study of those prior art processes quantitatively in detail, analyzing the steps of separating excess ammonia and decomposing/separating ammonium carbamate and returning those products into the reaction zone, individually and comprehensively in connection with the properties of the treated substances and investigating reationalization of the steps of urea production. It has been found, according to the process of the present invention, that the efficiency of the decomposition and separation can be improved unexpectedly as compared with those obtained by known processes wherein unconverted ammonium carbamate is decomposed and thereby separated under a high pressure.

If the technique of separating the gas formed by the decomposition from the liquid phase of the effluent from the reactor under a high pressure is improved, the decomposition is also accelerated consequently and favorable results can be obtained. For reducing the loss of power used for maintaining the pressure required in the synthesis zone and also for utilizing most of the high energy level of the process flow, ammonium carbamate is decomposed and thereby separated by introducing the effluent from the synthesis zone into an ammonium carbamate decomposition/separation zone without effecting pressure reduction. For accelerating the separation of the decomposed gas from the liquid phase under the high pressure, the free surface of the liquid effluent is enlarged in the process of the present invention. Residence time sufficient for the decomposition and separation is provided. In a stage in which the concentration of the unconverted substances is high and in which decomposition and separation are relatively large in amount, the decomposition and separation are effected by supplying only heat for effecting ammonium carbamate decomposition or, alternatively, by using starting ammonia as a stripping gas and the gaseous mixture thus separated out is removed therefrom so as to prevent re-dissolution of the gaseous mixture separated from the liquid phase and re-formation of ammonium carbamate. In a stage in which the concentration of the unconverted substances is low and in which decomposition and separation are relatively small in amount, ammonium carbamate remaining in the urea solution is reduced in amount by employing both supply of heat for ammonium carbamate decomposition and stripping with starting carbon dioxide.

The combination of the above described means brings about a multiplied effect.

The absence of the gas decomposed and thereby separated from the subsequent step in the stage in which the gaseous mixture formed by decomposition and separation is large in amount is advantageous for the decomposition/separation of ammonium carbamate and for the separation of excess ammonia.

By providing the decomposition/separation treatment in the first step, load in the step the of the decomposition/separation in which carbon dioxide is used as the stripping gas becomes low, both the decomposition and separation in this step become effective and the remaining ammonium carbamate is reduced in amount, whereby the load in the subsequent step of purifying the urea solution under reduced pressure is reduced remarkably.

The present invention provides a process for synthesizing urea by reacting ammonia with carbon dioxide, as starting materials, in a reactor, at a high temperature, under a high pressure, to obtain urea and unconverted materials, decomposing the unconverted materials, separating the decomposition products from urea, i.e. the intended product, and returning them into the reactor, wherein the effluent containing urea, ammonium carbamate, excess ammonia and water from the reactor is introduced in a first heater to decompose and thereby to separate the excess ammonia and ammonium carbamate from the liquid phase under substantially the same pressure as in the reactor; then the liquid effluent from the first heater is introduced in a second heater to separate remaining excess ammonia and also to decompose ammonium carbamate in the presence of starting carbon dioxide which acts as a stripping gas, thereby separating the same from the liquid phase under substantially the same pressure as in the reactor; the liquid effluent from the second heater is sent into a step of purifying the urea solution under a low pressure; and the gaseous, separated effluents discharged from the first and the second heaters are returned into the reactor.

As in the first and second heaters, there are used heat exchangers of the falling thin film type in which the separation of ammonia and decomposition of ammonium carbamate are accelerated. The gaseous effluents from the first and the second heaters are sent into the reactor together with the solution returned from the urea purification step operated under low pressure. The ratio of the amount of the unconverted substances which are decomposed and/or separated in the first and the second heaters and distilled from them is 30–80%, preferably 50–70%, in the first heater and 20–70%, preferably 30–50%, in the second heater.

It is important in the process of the present invention that multiplication of decomposition and separation of the unconverted components under high pressure is realized by providing separation of gaseous effluent from the process flow between the first heater and the second heater. Therefore, a third heater may be used to provide the separation of gaseous effluent not in one step but in two steps, if the cost of the equipment makes that permissible. It is important to minimize outflow of substances other than the aqueous urea solution from the high pressure system under substantially the same pressure as in the urea synthesis, which comprises the reactor, first and second heaters and a mixer for collecting the gaseous effluents from those heaters.

In oder to minimize the amount of outflow of said other substances from the high pressure system, plural heaters are provided, gaseous effluents from those heaters are returned to the reactor and unconverted substances are selectively retained in the high pressure system.

Except for the aqueous urea solution, the unconverted substances are not transferred to a low energy state and, therefore, a remarkable effect can be obtained.

In the accompanying FIG. 1 flow sheet, the invention is illustrated as an example, which is given by way of illustration and not of limitation.

DETAILED DESCRIPTION

Figure 1:
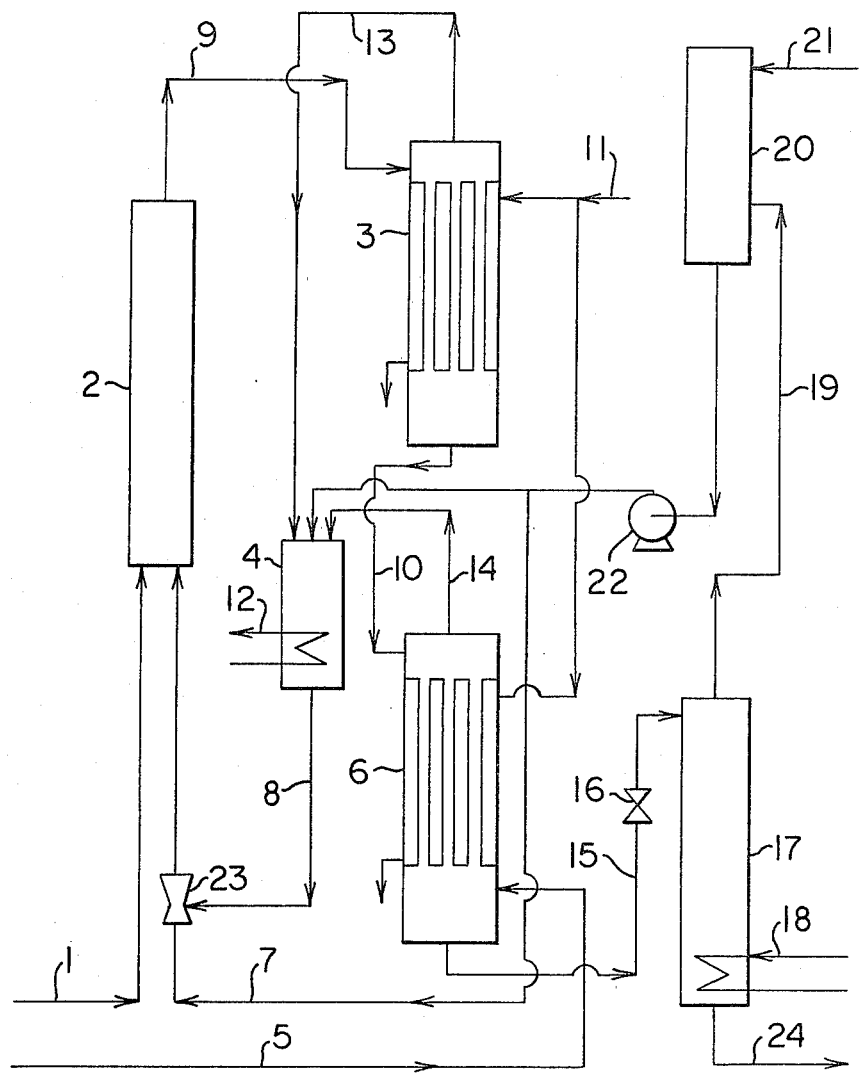
FIG. 1 is a flow sheet showing steps of the process of the present invention.

The process of the present invention will be illustrated with reference to FIG. 1.

Pressurized starting ammonia is introduced in a reactor 2 for urea synthesis through a pipe 1.

It is also possible to introduce the starting ammonia, not directly into the reactor 2, but rather, first into a first heater 3 to use it as a stripping gas therein and then to introduce the same into the reactor through a mixer 4.

Starting carbon dioxide is used as the stripping gas supplied in a lower part of a second heater 6 through a pipe 5 and then introduced into the reactor 2 through the pipe 14, the mixer 4, and the pipe 8.

A recycle liquid obtained by separating and thereby recovering ammonium carbamate, etc. remaining in the aqueous urea solution under a pressure lower than the urea synthesis pressure is also introduced in the reactor 2 through a pipe 7.

The recycle liquid of pipe 7 flows into the injector 23, together with the high pressure returning flow of the unconverted substances supplied through a pipe 8 from the mixer 4, and thence flows into the reactor 2.

A part of the recycle liquid may flow through the mixer 4 as a side flow.

Urea is formed in the reactor 2 at a high temperature under a high pressure, in the presence of excess ammonia (i.e. at a molar ratio of $NH_3$ to $CO_2$ of, for example, 4:1). Urea is introduced together with unconverted ammonium carbamate, excess ammonia and water, as an effluent from the reactor 2, into the first heater 3 through a pipe 9 and then into a second heater 6 through a pipe 10. The unconverted ammonium carbamate and excess ammonia in the effluent are separated as a gaseous mixture from the liquid phase flow which is in the form of a falling thin film under substantially the same pressure as in the urea synthesis.

In the second heater 6, the starting carbon dioxide is utilized as the stripping gas for accelerating the separation of the gaseous mixture as described above. Into the first and the second heaters, steam for heating is supplied through pipe 11 as needed.

In the mixer 4, ammonia reacts with carbon dioxide vigorously to generate a large amount of heat of reaction. The heat of reaction is recovered as steam through a pipe 12.

The thus-recovered heat of reaction generated at a high energy level in the mixer 4 can be used, if desired, as a direct heat source in an aqueous urea solution purification step under low pressure, for example, in a heating device 18 to exhibit a higher efficiency.

A description will be made on the first and second heaters which are important parts in the process of the present invention. In the heater 3, the effluent from the reactor 2 flows down in the form of thin films on the inner surfaces of numerous vertical tubes. By the heat of the heating media supplied as needed on the outer surfaces of the vertical tubes, the remaining ammonium carbamate unconverted into urea is decomposed into ammonia and carbon dioxide, which are separated from the liquid effluent, together with excess ammonia and these gases are introduced into the mixer 4 through a pipe 13.

As the vertical tubes in the heater 3, cylindrical tubes or double fluted tubes may be used. The separated gaseous mixture flows in countercurrent flow with respect to the liquid effluent flowing downward, as is shown by the position of pipe 13 in FIG. 1 or, alternatively, it may flow concurrently with the liquid effluent by changing the position of pipe 13.

Either a countercurrent or a concurrent flow can be selected easily, since the separated gaseous mixture is taken out, not just once, but twice, through pipes 13 and 14 in the decomposition/separation steps, under substantially the same pressure as in the reactor and can not stay in a large amount locally in the heaters.

As heaters are used at the two decomposition/separation steps, the difference in quantity of liquid between the inlet and outlet of each heating tube is small and a stable falling thin film is thus maintained favorably.

It is an advantage of the present invention that either a countercurrent flow by which the required residence time is secured at a low flowing-down velocity or a concurrent flow by which high rates of mass and heat transfer are attained at a high flowing-down velocity may be selected freely.

By virtue of those merits, the unconverted substances can be retained highly selectively in the high pressure system.

The effluent from the reactor which reaches the bottom of the heater 3 is supplied into an upper part of the second heater 6 through the pipe 10 and flows downwards in the form of thin films on the inner surfaces of the numerous vertical tubes. Ammonium carbamate is further decomposed by heat supplied by the heating media fed as needed onto the outer surfaces of the vertical tubes. It is subjected to stripping by the starting carbon dioxide fed through the pipe 5. The gaseous mixture expelled from the effluent from the reactor in the heater 6 is sent into the reactor 2 through a pipe 14 via the mixer 4.

Thus, the substances remaining unconverted into urea, including the excess ammonia, are prevented from outflowing from the high pressure system and the retained therein. Only the aqueous urea solution flows out selectively.

If the entire high pressure system is regarded as the reactor for urea synthesis, this reactor has internally a mechanism of recycling the unconverted substances as starting materials and produces urea at a conversion higher than the quilibrium conversion.

The effluent from the reactor then reaches the bottom of the heater 6. Thereafter, it is sent to a pressure reducing valve 16 through a pipe 15 and the pressure is reduced to lower than the urea synthesis pressure. It is then introduced in a decomposition device 17, in which the remaining unconverted substances are removed by decomposition with a heating media supplied through a pipe 18 under the pressure lower than the urea synthesis pressure, thereby purifying the aqueous urea solution.

The substances removed from the solution in the decomposition device 17 are introduced into an absorption device 20 through a pipe 19 and dissolved in an absorbing liquid supplied through a pipe 21. The liquid thus formed is then pumped with a pump 22 and is introduced into an injector 23 through a pipe 7. The liquid merges the effluent from the mixer 4 and flows into the reactor 2. The aqueous urea solution purified in the decomposition device 17 is sent into the subsequent purification step (not shown in the figure) through a pipe 24.

Figure 2:
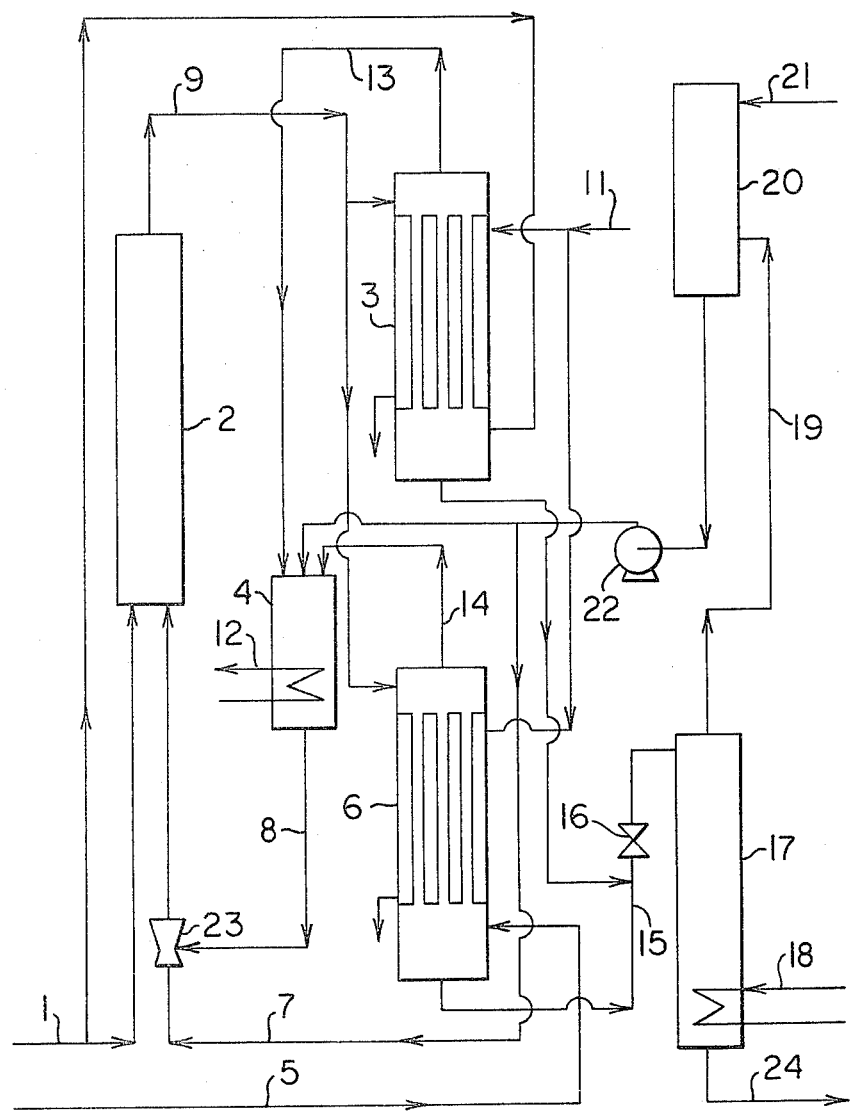
FIG. 2 is a flow sheet showing steps of a process to be compared with the process of the present invention.

For comparison with said process of the present invention, another process is illustrated in FIG. 2.

This process constitutes a different process comprising the combination of two known processes.

As compared with a case of employing only one known process, utility cost of urea production can be improved. But, as will be easily understood from the construction of this process, the effect of multiplication achieved by the process of the present invention cannot be obtained thereby.

A difference between FIGS. 1 and 2 is that heaters 3 and 6 in FIG. 2 are positioned in parallel to share the load.

Effects achieved by the process of the present invention are shown below as compared with those of a conventional process:

| | Conventional process | Process of the present invention |
|---|---|---|
| Urea production (t/day) | | 1,000 |
| Starting ammonia (t/day) | | 566 |
| Starting carbon dioxide (t/day) | | 735 |
| Pressure in reactor 2 (Kg/cm$^2$G) | | 200 |
| Temperature in reactor 2 (°C.) | | 191 |
| Pressure in decomposition device 17 (Kg/cm$^2$G) | | 17 |
| Temperature of fluid in pipe 24 (°C.) | | 165 |
| Heating steam consumption | | |
| 25 Kg/cm G Steam (t/t urea) (for the first and the second heaters) | — | 0.66 |
| 12 Kg/cm G Steam (t/t urea) (for the decomposition device) | 0.63 | — |
| (for others) | 0.32 | 0.02 |
| Subtotal (t/t urea) | 0.95 | 0.68 |
| 5 Kg/cm G recovered steam (t/t urea) | — | 0.37 |
| Total (t/t urea) | 0.95 | 0.31 |
| Cooling water (t/t urea) | 85 | 50 |
| Electric power (KWH/t urea) | 150 | 142 |

We claim:

1. In a urea synthesis process in which ammonia and carbon dioxide are reacted in a reactor, at an elevated temperature and pressure, to form a urea synthesis effluent stream containing urea, ammonium carbamate, ammonia and water, the improvement which comprises: passing said effluent stream downwardly through a first heating zone which is maintained at substantially the same pressure as said reactor and which is externally heated so as to decompose a large amount of said ammonium carbamate to form ammonia and carbon dioxide and to distill off ammonia and carbon dioxide gases; separating the effluent stream in said first heating zone into a first gas phase containing ammonia and carbon dioxide and a first liquid phase containing said urea, said water and reduced amounts of ammonium carbamate and ammonia, then passing said first liquid phase downwardly through a second heating zone which is maintained at substantially the same pressure as said reactor and which is externally heated so as to decompose ammonium carbamate in said first liquid phase to form ammonia and carbon dioxide and to distill off ammonia and carbon dioxide gases, and simultaneously contacting said first liquid phase with $CO_2$ stripping gas fed into said second heating zone from an external source thereof whereby to remove ammonia from said first liquid phase; separating said first liquid phase in said second heating zone into a second gas phase containing ammonia and carbon dioxide and a second liquid phase of an aqueous urea solution; then reducing the pressure of said second liquid phase and feeding same through a urea purification stage which is at a lower pressure than said reactor whereby to obtain a purified aqueous urea solution; and continuously maintaining said first gas phase and said second gas phase substantially at a pressure of said reactor and feeding said first gas phase and said second gas phase into said reactor.

2. A urea synthesis process as claimed in claim 1 in which said first heating zone and second heating zone each comprise a plurality of externally heated vertical tubes and wherein said effluent stream flows downwardly in the form of thin films on the internal surfaces of said vertical tubes of said first heating zone and said first liquid phase flows downwardly in the form of thin films on the inernal surfaces of said vertical tubes of said second heating zone.

3. A urea synthesis process as claimed in claim 2 in which said first gas phase is removed from the upper end of said first heating zone, said first liquid phase is removed from the lower end of said heating zone, said second gas phase is removed from the upper end of said second heating zone and said second liquid phase is removed from the lower end of said second heating zone.

4. A urea synthesis process as claimed in claim 2 in which said first gas phase and said first liquid phase are separately removed from the lower end of said first heating zone, and said second gas phase and said second liquid phase are separately removed from the lower end of said second heating zone.

5. A urea synthesis process as claimed in claim 1 or claim 2 in which the conversion of ammonium carbamate to urea in said reactor is from 50 to 75 percent and wherein from 30 to 80 percent of said ammonium carbamate in said effluent stream is decomposed and separated in said first heating zone and from 20 to 70 percent of said ammonium carbamate in said effluent stream is decomposed and separated in said second heating zone.

6. A urea synthesis process as claimed in claim 1 or claim 2 in which the conversion of ammonium carbamate to urea is from 50 to 75 percent and wherein from 50 to 70 percent of said ammonium carbamate in said effluent stream is decomposed and separated in said first heating zone and from 30 to 50 percent of said ammonium carbamate in said effluent stream is decomposed and separated in said second heating zone.

7. A urea synthesis process as claimed in claim 1 or claim 2 in which in said first heating zone, said effluent stream is contacted with a stream of ammonia gas effective to strip said gaseous ammonia and gaseous carbon dioxide formed by decomposing said ammonium carbamate.

8. A urea synthesis process as claimed in claim 1 in which in said urea purification stage, said second liquid phase is heated to decompose any remaining ammonium carbamate present therein, removing a third gas phase from said urea purification stage and absorbing said third gas phase in an absorbing liquid.

9. A urea synthesis process as claimed in claim 1 or claim 2 in which said first and second gas phases are mixed together in a mixing vessel and then the resultant mixture thereof is injected into said reactor.

10. A urea synthesis process as claimed in claim 9 in which in said urea purification stage, said second liquid phase is heated to decompose any remaining ammonium carbamate present therein, removing a third gas phase from said urea purification stage and absorbing said third gas phase in an absorbing liquid, and mixing said absorbing liquid with said first and second gas phases in said mixing vessel.

* * * * *

UNITED STATES PATENT AND TRADEMARK OFFICE
CERTIFICATE OF CORRECTION

PATENT NO. : 4 334 096
DATED : June 8, 1982
INVENTOR(S) : Keizo Konoki et al

It is certified that error appears in the above—identified patent and that said Letters Patent is hereby corrected as shown below:

```
Column 6, line 60; change "a" to ---the---.
Column 6, line 64; after "and" insert ---said---.
Column 7, line  2; change "inernal" to ---internal---.
Column 7, line  7; after "said" (first occurrence)
                   insert ---first---.
```

Signed and Sealed this

Seventh Day of September 1982

[SEAL]

Attest:

GERALD J. MOSSINGHOFF

Attesting Officer

Commissioner of Patents and Trademarks